(12) United States Patent
Moon et al.

(10) Patent No.: US 11,771,642 B2
(45) Date of Patent: Oct. 3, 2023

(54) PUMPING TYPE TOOTHPASTE COMPOSITION

(71) Applicant: LG Household & Health Care Ltd., Seoul (KR)

(72) Inventors: Kyo-Tae Moon, Daejeon (KR); Ji-Hye Lee, Daejeon (KR); Seong-Lok Hwang, Daejeon (KR); Won-Ho Ha, Daejeon (KR); Aram You, Daejeon (KR)

(73) Assignee: LG Household & Health Care Ltd.

( * ) Notice: Subject to any disclaimer, the term of this patent is extended or adjusted under 35 U.S.C. 154(b) by 426 days.

(21) Appl. No.: 16/617,312

(22) PCT Filed: Feb. 19, 2018

(86) PCT No.: PCT/KR2018/002032
§ 371 (c)(1),
(2) Date: Nov. 26, 2019

(87) PCT Pub. No.: WO2018/221837
PCT Pub. Date: Dec. 6, 2018

(65) Prior Publication Data
US 2020/0360265 A1  Nov. 19, 2020

(30) Foreign Application Priority Data

May 31, 2017 (KR) .................... 10-2017-0067843
May 31, 2017 (KR) .................... 10-2017-0067866

(51) Int. Cl.
| | | |
|---|---|---|
| A61Q 11/00 | (2006.01) | |
| A61K 8/18 | (2006.01) | |
| A61K 8/92 | (2006.01) | |
| A61K 8/19 | (2006.01) | |
| A61K 8/67 | (2006.01) | |
| A61K 8/73 | (2006.01) | |
| A61K 8/86 | (2006.01) | |
| B05B 11/00 | (2023.01) | |

(52) U.S. Cl.
CPC ............ *A61K 8/922* (2013.01); *A61K 8/19* (2013.01); *A61K 8/678* (2013.01); *A61K 8/73* (2013.01); *A61K 8/86* (2013.01); *B05B 11/0037* (2013.01); *A61K 2800/28* (2013.01); *A61K 2800/49* (2013.01); *A61K 2800/87* (2013.01)

(58) Field of Classification Search
CPC .... A61Q 11/00; A61K 2800/92; A61K 8/042; A61K 8/25; A61K 2800/28; A61K 2800/48; A61K 2800/262; A61K 8/92; A61K 2800/596; A61K 2800/5422; A61K 2800/49; A61K 2800/42
See application file for complete search history.

(56) References Cited

U.S. PATENT DOCUMENTS

| | | | |
|---|---|---|---|
| 5,059,417 A | 10/1991 | Williams et al. | |
| 5,178,869 A | 1/1993 | Ebine et al. | |
| 5,252,313 A | 10/1993 | Collins et al. | |
| 7,166,272 B2 | 1/2007 | Fujisawa | |
| 2003/0133882 A1* | 7/2003 | Kostinko | ............. C01B 33/193 424/49 |
| 2016/0151255 A1 | 6/2016 | You et al. | |
| 2017/0119634 A1 | 5/2017 | Zeng et al. | |
| 2017/0151580 A1* | 6/2017 | Toh | ........................ A45D 34/04 |
| 2017/0246097 A1 | 8/2017 | Calvert et al. | |
| 2018/0214440 A1* | 8/2018 | Coates | .................... A61Q 11/00 |

FOREIGN PATENT DOCUMENTS

| | | | |
|---|---|---|---|
| CN | 1079383 A | 12/1993 | |
| CN | 1237894 A | 12/1999 | |
| CN | 1745743 A | 3/2006 | |
| CN | 104905987 A | 9/2015 | |
| CN | 105792798 A | 7/2016 | |
| EP | 0251542 A2 * | 1/1988 | |
| EP | 0436284 A1 | 7/1991 | |
| EP | 0464913 A1 | 1/1992 | |
| EP | 1061892 A1 | 12/2000 | |
| JP | H4-253906 A | 9/1992 | |
| JP | H07126131 A | 5/1995 | |
| JP | 2001002157 A | 1/2001 | |
| JP | 4076874 B2 | 4/2008 | |
| JP | 2009-084277 A | 4/2009 | |
| JP | 2009-519235 A | 5/2009 | |
| KR | 100129819 B1 | 4/1998 | |
| KR | 20140146983 A | 12/2014 | |
| KR | 20140146986 A | 12/2014 | |
| WO | 9822079 A1 | 5/1998 | |
| WO | 9947108 A1 | 9/1999 | |
| WO | WO-2007063507 A2 * | 6/2007 | ............... A61K 8/19 |
| WO | 2015016057 A1 | 2/2015 | |
| WO | 2016034519 A1 | 3/2016 | |
| WO | 2016034521 A1 | 3/2016 | |

OTHER PUBLICATIONS

Anonymous, "Liquid Type Baby Oral Clean With Apple Flavour", May 25, 2017, 3 pages, Database GNPD [Online] Mintel; Database Accession No. 4843295 *ABSTRACT*.
Extended European Search Report for Application No. 18809030.2 dated Feb. 9, 2021, 5 pages.
Thomson Scientific, Database WPI Week 201607, London, GB; AN 2015-710250 XP002801857, & CN 104 905987 A Guangzhou Libyenterprise Group Co. Ltd.), Sep. 16, 2015 *ABSTRACT*.
International Search Report for application No. PCT/KR2018/002032 dated Jun. 4, 2018, 2 pages.
Li, Luo et al., "Talking about the production of transparent toothpaste", Liuzhou Liangmianzhen Co., Ltd., Mar. 25, 2002, No. 1.

* cited by examiner

*Primary Examiner* — Tracy Liu
(74) *Attorney, Agent, or Firm* — Lerner David LLP

(57) ABSTRACT

The present disclosure relates to a pumping type toothpaste composition capable of being provided as contained in a pumping type container, and relates to a pumping type transparent toothpaste composition comprising or not comprising an abrasive. The pumping type toothpaste composition of the present disclosure has excellent commercial value due to its transparent formulation.

4 Claims, 1 Drawing Sheet

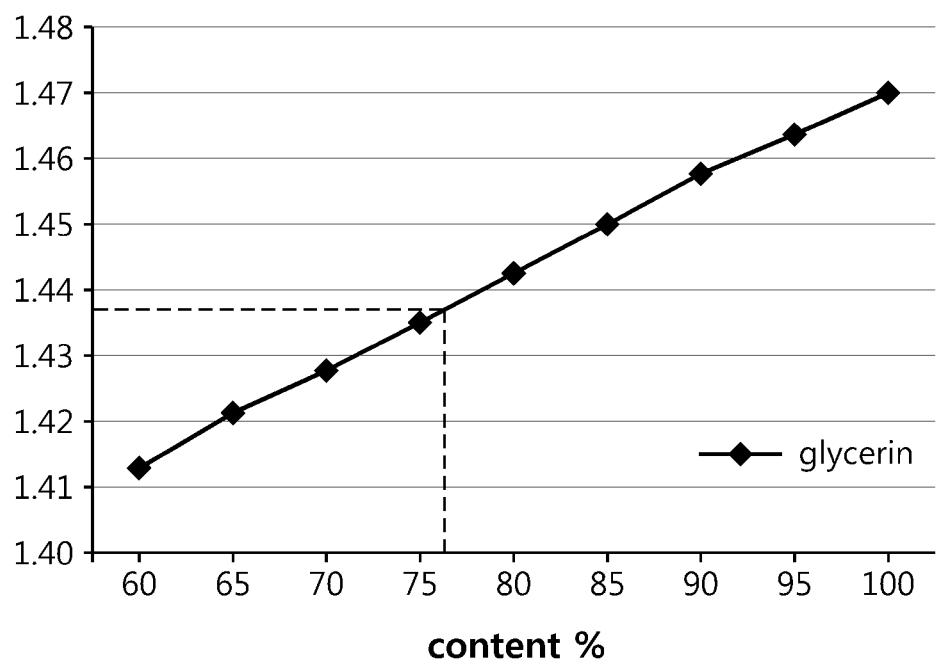

PUMPING TYPE TOOTHPASTE COMPOSITION

CROSS-REFERENCE TO RELATED APPLICATIONS

This application is a national phase entry under 35 U.S.C. § 371 of International Application No. PCT/KR2018/002032, filed Feb. 19, 2018, which claims priority to Korean Patent Application No. 10-2017-0067843 filed May 31, 2017, and Korean Patent Application No. 10-2017-0067866 filed May 31, 2017, the disclosures which are incorporated herein by reference.

TECHNICAL FIELD

The present disclosure relates to a toothpaste composition, and relates to a toothpaste composition in a transparent formulation, which is a toothpaste composition to be provided as contained in a pumping type container.

BACKGROUND ART

Toothpaste compositions commonly used for cleaning mouth and teeth include pastes, powders, gels/mucus or liquids, and their use and handling have certain advantages and disadvantages.

A paste type toothpaste originally developed in Colgate, USA, was sold in aluminum tubes and such aluminum tubes were still in use by the 1970s. The container of this paste type toothpaste has been developed as a laminated film material of aluminum as in modern times, and this is the development of polymer and polymer processing technology. However, this tube type of toothpaste has many inconveniences, for example, having problems of having high viscosity, being likely to cause damage to tooth enamel layers due to an abrasive ingredient, being inconvenient to squeeze during use as well as leaving residual toothpaste in a container to be discarded because products in the container cannot be used completely, and causing environmental pollution. In order to improve the releasability of such toothpaste and the like, a liquid toothpaste product having the flowing property in a plastic container has been developed, but when the it flows too well, it is difficult to effectively deliver a drug in the toothpaste product to teeth and gums. Accordingly, it has been widely used as an oral gargle that performs functions of inhibiting oral bacteria and removing bad breath, but it could not exhibit an effect of sufficient brushing such as removal of plaque in oral cavity and removal of oral bacteria and the like due to a problem of lack of cleaning ingredients and easy flow. There has been an attempt to apply a vacuum pumping type of plastic container to discharge high viscosity of paste, which has been applied next in order to enhance the user convenience, and some products are on the market, but they have price problems and poor releasability of conventional paste toothpastes and the like. In addition, powders are inconvenient in use since their particles are sprayed or scattered during its use.

In addition, conventional tube type toothpaste is distributed as contained in an opaque tube, and therefore the transparency at a level that it is transparent when it is discharged on a toothbrush is sufficient, but the pumping type toothpaste is distributed as contained in a transparent pumping container, and therefore it should be transparent even in the inside of the container, and thus it is necessary to increase the transparency highly.

However, it is still difficult to achieve sufficient transparency only by the technology to make it look transparent by using a silica-based abrasive as a major abrasive and mixing so that the refractive index of the abrasive and the refractive index of added ingredients, which is the method that has been used for preparing a transparent toothpaste composition conventionally.

DISCLOSURE

Technical Problem

Accordingly, a problem to be solved by the present disclosure is to solve the aforementioned problem, and provide a pumping type transparent toothpaste composition which can be provided as contained in a pumping type container.

More specifically, the present disclosure is to provide a pumping type toothpaste composition which is substantially free of abrasives, or comprises an abrasive, but in a transparent formulation.

Technical Solution

Transparent Pumping Type Toothpaste Composition not Comprising an Abrasive

One aspect of the present disclosure is to provide a pumping type transparent toothpaste composition which can be provided as contained in a pumping type container, and more specifically, a pumping type toothpaste composition in a transparent formulation which is substantially free of abrasives.

Conventionally, tube type toothpaste is distributed as contained in an opaque tube, and therefore transparency at a transparent level when discharged on a toothbrush is sufficient, but pumping type toothpaste is distributed as contained in a pumping container, and therefore it should look transparent even in the inside of the container, and thus it is necessary to increase the transparency highly.

Accordingly, it is still difficult to achieve sufficient transparency only by the technology to make it look transparent by using a silica-based abrasive as a major abrasive and mixing so that the refractive index of the abrasive and the refractive index of added ingredients, which is the method that has been used for preparing a transparent toothpaste composition conventionally.

The present inventors have confirmed that a pumping type transparent toothpaste composition in a transparent formulation can be prepared, when using a surfactant having HLB 14~23 as a solubilizer without using an abrasive, in a pumping type transparent toothpaste composition contained in a pumping type container, thereby completing the present disclosure.

In the specification according to the present disclosure, the term 'pumping type' means a structure capable of releasing contents stored inside of a container to the outside through a discharge port by pump action using a pushing member of the container. Specifically, it means a structure of releasing a toothpaste composition inside of a container to the outside of the container through pump action of a piston to use, and in other words, by the pump action, contents can be released from the inner bottom of the container to the outside by a piston equipped inside of the container.

The pumping type transparent toothpaste composition according to the present disclosure is provided for example, in a gel form.

In the specification according to the present disclosure, the term 'gel form' is used as a concept to distinguish from conventional liquid toothpaste in a dilute form and a paste-type toothpaste having high viscositye. The gel form is a formulation to be distinguished from the conventional liquid formulation, and means a formulation having a greater degree of stickiness than the liquid toothpaste and is viscous. The toothpaste in a gel form of the present disclosure means a formulation that is elastic and firmer than the liquid toothpaste. In addition, the gel toothpaste of the present disclosure has fluidity due to lower viscosity than a paste type of toothpaste and can be easily discharged to the outside due to flowability.

In the specification according to the present disclosure, the term 'elasticity' means a property that an object deformed by an external force tries to return to its original shape when the force is removed, and it has been used as a broad concept meaning a property of an object that is intended to maintain its original form. In other words, it has been used as a broad meaning including all properties to intend to maintain the original shape after discharging a toothpaste composition from a discharge port.

The present disclosure provides a pumping type transparent toothpaste composition contained in a pumping type container, which is a pumping type transparent toothpaste composition that comprises a solubilizer, but is substantially free of abrasives.

The pumping type transparent toothpaste composition according to the present disclosure comprises a solubilizer, and uses a surfactant having HLB 14~23 as the solubilizer.

Herein, the solubilizer solubilizes a substance having a low solubility to water, and a surfactant having HLB 14~23 is used.

The HLB (Hydrophile-Lipophile Balance) is a value representing the degree of affinity of a surfactant to water and oil, and the smaller the value of HLB is, the stronger the lipophilicity is as a whole molecule, and the bigger the value is, the stronger the hydrophilicity is. The HLB formula is as follows:

$$HLB = 20 \times \text{molecular weight of hydrophilic groups} / \text{total molecular weight}$$

Any surfactant having HLB 14~23 which has been known to be used for a toothpaste composition in the art can be used as a solubilizer, but for example, it may include polyglyceryl-3-methyl glucose distearate, Oleth-10, Oleth-10/polyoxyl 10 oleyl ester NF, cereth-10, PEG-8 laurate, cocamide MEA, polyoxyethylene hydrogenated castor oil-40 (HCO 40), polyoxyethylene hydrogenated castor oil-60 (HCO 60), poloxamer 184, poloxamer 407, or a mixture thereof, or the like, and preferably, polyoxyethylene hydrogenated castor oil-40 (HCO 40), poloxamer 407, or a mixture thereof may be used.

The polyoxyethylene hydrogenated castor oil-40 (HCO 40) is a non-ionic surfactant and it may be prepared by various preparation methods known in the art, and for example, it may be synthesized by addition polymerization of ethylene oxide (EO) to hydrogenated castor oil that a hydrogen is added to double bond of castor oil, or a commercially available product may be used. (HLB is about 12.5)

The poloxamer 407 is a non-ionic surfactant, and is a PEG-PPG-PEG block copolymer having a molecular weight of PPG block (polyoxypropylene molecular mass) of 4,000 g/mol and having 70% PEG (polyoxyethylene) content.

Herein, the content of the solubilizer may be comprised in an amount of 0.7-3% by weight, more preferably 1.3-2.5% by weight, much more preferably 1.3-2.2% by weight, based on the total weight of the composition. When using a solubilizer in the above range content, a toothpaste composition in a transparent formulation may be prepared.

In addition, the toothpaste composition according to the present disclosure is substantially free of abrasives.

As can be confirmed in specific examples of the present disclosure, even if a solubilizer is added, but when an abrasive is comprised, a toothpaste composition in a transparent formulation cannot be prepared.

In the specification of the present disclosure, the term 'substantially free' means comprising in an amount of less than 5% by weight, preferably, 1% by weight or less, more preferably, 0.1% by weight or less, most preferably 0% by weight (namely, not comprising at all), based on the total weight of the composition.

Herein, the 'abrasive' is a substance functioning of removing oral plaque, and it is necessarily used for increasing the efficiency of removal of dental plaque and removing hard foreign substances and the like, and Mohs hardness represents a value of about 3~6.

The abrasive may include all used as an abrasive of a toothpaste composition in the art, and for example, includes calcium hydrogen phosphate, precipitated silica, fumed silica, colloidal silica, zeolite, calcium carbonate, hydrated alumina, kaolin, cellulose and mixtures thereof, but not limited thereto.

The toothpaste composition according to the present disclosure may further comprise a fragrance ingredient, a sweetening agent, a pharmaceutical agent, a pH adjusting agent, a preservative, a binding agent, a foaming agent, a whitening agent, or the like, other than a binding agent, as ingredients commonly used as a toothpaste composition in the art, depending on their reproduction and use purposes.

The binding agent may use any one selected from the group consisting of sodium carboxymethyl cellulose, carbomer, carrageenan, xanthan gum, aqueous polyvinyl acryl resin, silica for thickening, aluminum silicate, salt of polyacrylate and a mixture thereof. This binding agent may be used alone or as mixed two kinds or more, and preferably, xanthan gum is used.

Preferably, the toothpaste composition according to the present disclosure is provided as a pumping type transparent toothpaste composition, and therefore it is preferable to comprise hydrophilic colloid comprising carboxymethyl cellulose, sodium alginate, xanthan gum, or a mixture thereof, and it is preferable to comprise a lubricant (polyol, glycerin, etc.) for preventing blocking a discharge port by drying. In addition, a non-aqueous ingredient including a fragrance ingredient, vitamin E or a mixture thereof may be comprised.

The toothpaste composition according to the present disclosure is provided as a pumping type transparent toothpaste composition, and therefore it is preferable to comprise a non-aqueous ingredient including a flavoring, vitamin E or a mixture thereof.

The hydrophilic colloid may provide appropriate viscosity of toothpaste, and the lubricant means a substance acting to reduce friction between two sides sliding in contact with each other, and the lubricant lubricates, thereby playing a role in preventing abrasion of a piston by a raw material (solid such as an abrasive) showing wear properties contained in the toothpaste composition of the present disclosure. The lubricant may comprise for example, any one selected from the group consisting of polyethylene glycol, glycerol, propylene glycol, ethylene glycol, polypropylene glycol and a mixture thereof, but not limited thereto. Preferably, it may comprise any one selected from the group consisting of polyethylene glycol 200 to 600, glycerol, propylene glycol, ethylene glycol, polypropylene glycol and a mixture thereof. Preferably, as a liquid lubricant, petroleum oil, animal and vegetable oil, synthetic lubricating oil, and the like may be used, and most preferably, in an aspect of stability and excellent usability of the composition, liquid polyol or polyol, glycerin or a mixture thereof may be used. Otherwise, the lubricant is not limited to liquid polyol, and it may include a high molecular weight of polyol like polyethylene glycol or polypropylene glycol which has a polymer form, which can be present in a solid state at a room temperature by intramolecular interaction of polymers over a certain molecular weight, but can be liquefied by controlling the preparation temperature and can be maintained in a stable state when manufactured.

In the composition of the present disclosure, a fragrance ingredient and a sweetening agent may be added to consumers' preference. The fragrance ingredient remains in the oral cavity and allows to maintain a sense of freshness by continually emitting fragrances.

As the fragrance ingredient, mint like peppermint, spearmint, etc., wintergreen, methyl salicylate, eugenol, melon, strawberry, orange, vanillin, or the like may be used. In general, the fragrance ingredient may be used in a range of 0.001 to 10% by weight based on the total weight of the composition.

In addition, for overcoming the basic taste that the formulation may have, a sweetening agent may be added in the composition of the present disclosure. The sweetening agent may play a role in sustaining occurrence of saliva by providing the taste continuously while remaining in the oral cavity.

As the sweetening agent, one kind or two mixed kinds of saccharin, sucralose, sugar, xylitol, sorbitol, lactose, mannitol, maltitol, erythritol, aspartame, taurine, saccharin salt, D-tryptophan, and the like may be used. Among saccharin salts, sodium saccharin is most widely used. The amount of the sweetening agent is generally in a range of 0.001 to 20% by weight based on the total weight of the composition or 0.001 to 5% by weight based on the total weight.

As the pharmaceutical agent used for oral hygiene, ingredients having an effect of cavity prevention, gum disease prevention, plaque deposition prevention, whitening, or the like may be used. The pharmaceutical agent used for cavity prevention includes a compound approved as a safe substance by U.S. Food and Drug Administration, including fluoride ion. The compound which can be used as a source of the fluoride ion includes sodium fluoride, sodium monofluorophosphate, stannous fluoride, and ammine fluoride. The content of fluorine may differ in usage depending on countries, but preferably, it is common to use a mixture of 1 kind or 2 kinds or more of sources so as to have a fluorine ion concentration in a range of 850 to 1500 ppm. A recalcification agent may also act as a cavity preventing agent. The recalcification plays a role in regenerating and restoring hydroxyapatite that is a major component of teeth. The major component of hydroxyapatite consists of divalent calcium cation and phosphate anion. Accordingly, one which provides a calcium ion and a phosphate ion simultaneously or contains a calcium divalent ion or one kind or more of phosphate anions so as to shift oral chemical equilibrium towards the formation of hydroxyapatite may be used as the recalcification agent. The substance providing calcium and phosphorus includes raw material hydroxyapatite, dicalcium phosphate, calcium chloride, casein phospeptide, calcium glycerophosphate, monosodium phosphate, sodium diphosphate, sodium triphosphate, monopotassium phosphate, dipotassium phosphate, tripotassium phosphate, or the like. Generally, it is preferable to use the recalcification agent in a range of 0.001 to 20% by weight or 0.001 to 5% by weight based on the total composition. When it is less than 0.001% by weight, the recalcification effect is reduced, and when it is more than 20% by weight, properties which the formulation originally has are lost. One of purposes of using an oral hygiene item is to alleviate a proceeding gum disease, as well as, to prevent a gum disease in advance, by sterilization or anti-inflammation action against harmful microorganisms present in the oral cavity. For this purpose, isopropyl methyl phenol, cyclohexidin, cetyl pyridinium chloride, triclosan, xanthorrhizol, or the like, which is known as an antimicrobial agent, may be used, and for anti-inflammation action, vitamins (e.g. vitamin E) and enzymes, aminocaproic acid, allantoin and its derivative and the like may be used. The pharmaceutical agent may be contained in an amount of 0.005% by weight to 5% by weight. When the content of the pharmaceutical agent is less than 0.005, it is difficult to show a medicinal effect, and when it is contained more than 5% by weight, there is a disadvantage of changing the taste of the basic base. Peroxide, carbamide peroxide, calcium peroxide or the like, which shows a whitening effect in addition to gum diseases, may be used, and to obtain a plaque deposition inhibition effect, sodium pyrophosphate, acidic sodium pyrophosphate, potassium pyrophosphate, sodium metaphosphate, or the like is used. In general, this pharmaceutical agent is used in a range of 0.001 to 10% by weight based on the total weight of the composition.

As the pH adjusting agent, phosphate, sodium phosphate, citrate, sodium citrate, succinate, sodium succinate, tartrate, sodium tartrate, or the like may be used, and the acidity of an oral composition is generally 5 to 8.

As the preservative, benzoic acid, methyl paraben, propyl paraben, sodium benzoate or the like may be used.

As the foaming agent, an anion, amphoteric and non-ionic surfactant of sodium alkylsulfate, sodium lauryl sulfate, alkyl sarcosinate, lauryl sarcosinate, cocoyl glutamate sodium salt, myristoyl glutamate sodium salt, cocamidopropyl betaine, sucrose fatty acid ester, sorbitan fatty acid ester, polyoxyethylene-polyoxypropylene block copolymer (poloxamer) may be used alone or as mixed two or more kinds.

As the whitening agent, titanium oxide is used, and generally, it is used in an amount of 0.1% to 2% by weight.

The method for preparing the toothpaste composition of the present disclosure may prepare according to the method for preparing commonly in the art.

For example, other ingredients except for an abrasive and selectively a pharmaceutical agent may be primarily mixed, wherein ingredients comprising a solubilizer and non-aqueous ingredients may be mixed, and next the abrasive and selectively a pharmaceutical agent may be secondarily mixed.

The toothpaste composition according to the present disclosure may be diverted into mouthwash, a denture cleansing agent, or the like.

The pumping type transparent toothpaste composition according to the present disclosure is provided as contained in a pumping type container.

The present disclosure provides pumping type toothpaste comprising the aforementioned pumping type transparent toothpaste composition, and a pumping type container in which the pumping type transparent toothpaste composition is contained.

Transparent Pumping Type Toothpaste Composition Comprising an Abrasive

Other aspect of the present disclosure is to provide a pumping type toothpaste composition which can be provided as contained in a pumping type container, and more specifically, a pumping type toothpaste composition which comprises an abrasive and is in a transparent formulation.

The present inventors have confirmed that a pumping type transparent toothpaste composition in a transparent formulation can be prepared, when an abrasive having a refractive index of 1.420-1.465 is comprised and a flavoring is solubilized and used by using a surfactant having HLB 12 or more, more preferably HLB 12-23, most preferably HLB 14-23, in the pumping type transparent toothpaste composition contained in a pumping type container, thereby completing the present disclosure.

The present disclosure provides a pumping type transparent toothpaste composition contained in a pumping type container, which comprises an abrasive having a refractive index of 1.420-1.465 and a solubilizer having HLB 12 or more, preferably HLB 12-23, more preferably HLB 14-23.

Herein, the 'abrasive' is a substance functioning of removing oral plaque, and it is necessarily used to increase the efficiency of removal of dental plaque and remove hard foreign substances and the like, and the abrasive comprised in the present disclosure preferably has a refractive index of 1.42-1.465.

So that the refractive index of the abrasive and the refractive index of the liquid raw material substantially match, the ingredients of cosmetic composition and the content of the ingredients may be determined, and the refractive index may be measured by any known method for measuring the refractive index, and for example, it may be conducted by a method of using an immersion refractometer, or a method for preparing a concentration showing 70% or more of light transmittance using a spectrophotometer, or the like, but not limited thereto.

Herein, the 'refractive index and refractive index substantially match' means that the difference between two refractive indexes is less than 1, less than 0.5, less than 0.1, less than 0.01, less than 0.001, most preferably, 0.

The abrasive may include all used as an abrasive of a toothpaste composition in the art without departing from the range of the refractive index, and for example, includes precipitated silica, fumed silica, colloidal silica, calcium hydrogen phosphate, zeolite, calcium carbonate, hydrated alumina, kaolin, cellulose and mixtures thereof, and preferably, a silica-based abrasive such as precipitated silica, fumed silica, colloidal silica, and the like may be used.

The content of the abrasive is 5 to 18% by weight based on the total weight of the composition. When the content of the abrasive is less than 5% by weight, the toothpaste cannot exhibit abrasivity and therefore it cannot have plaque detergency, and when it is over 18% by weight, it may difficult to be discharged in a pumping type container of the toothpaste composition.

Herein, the pumping type transparent toothpaste composition may further comprise a refraction adjusting agent, and the refraction adjusting agent is comprised to make the refractive index of the abrasive and the refractive index of the cosmetic composition similar, and for example, it may be polyethylene glycol, propylene glycol, glycerin, erythritol, xylitol, sorbitol, mannitol, lactitol, hydrogenated starch hydrolysates or a mixture thereof, and preferably, it is glycerin, but not limited thereto.

Herein, the pumping type transparent toothpaste composition may further a refraction adjusting agent and water, and preferably, the weight ratio of the refraction adjusting agent and water is 65:35 to 90:10. In addition, the weight ratio of the abrasive, refraction adjusting agent and water is 10-15:60-80:5-30, preferably 10-15:60-75:10-20, most preferably 14:65~70:16~21 as abrasive:refraction adjusting agent:water. The weight ratio is a weight ratio preferable to make refraction indexes of the solid ingredients such as the abrasive and the like and the liquid raw materials of the toothpaste composition similar, and when it is over the range of the weight ratio, a transparent formulation intended for the present disclosure is not implemented.

The pumping type transparent toothpaste composition comprises a solubilizer, and as the solubilizer, preferably, a surfactant having HLB 12 or more, more preferably, a surfactant having HLB 12-23, most preferably, a surfactant having HLB 14-23 is used.

Herein, the solubilizer is a substance which solubilizes a substance having a low solubility to water, and a surfactant having preferably HLB 12 or more, more preferably HLB 12-23, most preferably HLB 14-23 is used.

The formula of the HLB (Hydrophile-Lipophile Balance) is as described above.

Any surfactant having HLB 12 or more, preferably HLB 12-23, more preferably 14-23 which has been known to be used for a toothpaste composition in the art can be used as a solubilizer, but for example, it may include polyglyceryl-3-methyl glucose distearate, Oleth-10, Oleth-10/polyoxyl 10 oleyl ester NF, cereth-10, PEG-8 laurate, cocamide MEA, polyoxyethylene hydrogenated castor oil-40 (HCO 40), polyoxyethylene hydrogenated castor oil-60 (HCO 60), poloxamer 184, poloxamer 407, or a mixture thereof, or the like, and preferably, polyoxyethylene hydrogenated castor oil-40 (HCO 40), poloxamer 407, or a mixture thereof may be used.

The present inventors have confirmed that the effect of the invention is the best, particularly, in the aspect of transparency, when using HCO 40, poloxamer 407 alone or a mixture thereof, as the solubilizer. The HCO 40 and poloxamer 407 are as described above.

Furthermore, the content of the solubilizer may be 0.7 to 3% by weight, preferably 1 to 2.5% by weight, more preferably 1.3 to 2.2% by weight, based on the total weight of the composition. When the solubilizer is used in the content in the above range, a toothpaste composition in a transparent formulation may be prepared.

The toothpaste composition according to the present disclosure may further comprise ingredients commonly used in the toothpaste composition in the art, within the scope of not impairing the object of the present disclosure, and for example, it may further comprise a fragrance ingredient, a sweetening agent, a pharmaceutical agent, a pH adjusting agent, a preservative, a binding agent, a foaming agent, a whitening agent, or the like, and detailed description of them is as described above.

In addition, the method for preparing the toothpaste composition of the present disclosure may prepare according to the method for preparing in the art, and preferably, the present disclosure provides a method for preparing a pumping type transparent toothpaste composition comprising primarily mixing by adding a solubilizer into the non-aqueous ingredients, and secondarily mixing the abrasive and selectively pharmaceutical agent.

The toothpaste composition according to the present disclosure may be diverted into mouthwash, a dental cleansing agent, or the like, and that provided as contained in a pumping type transparent container is as described above.

Advantageous Effects

According to the present disclosure, a pumping type transparent toothpaste composition which can be provided as contained in a pumping type container is provided, and in particular, a toothpaste composition having excellent commercial value, which does not comprise an abrasive substantially or comprises an abrasive, but is in a transparent formulation, is provided.

BRIEF DESCRIPTION OF THE DRAWINGS

The following drawings accompanied herein illustrate preferable examples of the present disclosure, and serve to further understand the technical idea of the present disclosure together with the aforementioned disclosure, and thus the present disclosure should not be construed as being limited to the matters described in such drawings.

The FIGURE is a graph showing the refractive index according to the content of glycerin in water, for the pumping type transparent toothpaste composition according to the following Preparative example 2.

DETAILED DESCRIPTION OF THE EMBODIMENTS

Hereinafter, the present disclosure will be described with reference to the following examples and the like to describe the present disclosure in more detail. However, the examples according to the present disclosure can be modified into various other forms, and the scope of the present disclosure should not be construed as being limited to the examples described below. The examples of the present disclosure are provided illustratively in order to facilitate a specific understanding of the present disclosure.

Preparative Example 1 of Pumping Type Toothpaste Composition (1) Ingredients and Composition Ratio Toothpaste compositions of examples and comparative examples were prepared by the ingredients and composition ratios shown in the following Table 1. Other ingredients except for an abrasive such as silica or the like and a pharmaceutical agent were completely dispersed for primary mixing. Here, non-aqueous ingredients, vitamin E and a flavoring were primarily mixed by adding a solubilizer, HCO40, poloxamer 407, polysorbate 20, or octyldodeceth-16 together. Next, the abrasive such as silica or the like and the pharmaceutical agent were added and were mixed under vacuum to prepare toothpaste compositions. However, Comparative example 4 not using a solubilizer was prepared without the primary mixing process.

TABLE 1

|  | Example 1 | Example 2 | Example 3 | Comparative example 1 | Comparative example 2 | Comparative example 3 | Comparative example 4 | Compartive example 5 | Compartive example 6 |
| --- | --- | --- | --- | --- | --- | --- | --- | --- | --- |
| Precipitated silica | 0 | 0 | 0 | 5.00 | 5.00 | 5.00 | 0 | 0 | 0 |
| Glycerin | 45.00 | 45.00 | 45.00 | 45.00 | 45.00 | 45.00 | 45.00 | 45.00 | 45.00 |
| Sodium lauryl sulfate | 1.00 | 1.00 | 1.00 | 1.00 | 1.00 | 1.00 | 1.00 | 1.00 | 1.00 |
| HCO40 | 2.00 | 0 | 1.10 | 2.00 | 0 | 1.10 | 0 | 0 | 0 |
| Poloxamer 407 | 0 | 2.00 | 1.10 | 0 | 2.00 | 1.10 | 0 | 0 | 0 |
| Polysorbate 20 | 0 | 0 | 0 | 0 | 0 | 0 | 0 | 2.00 | 0 |
| Octyldodecet h-16 | 0 | 0 | 0 | 0 | 0 | 0 | 0 | 0 | 2.00 |
| Sodium saccharin | 0.20 | 0.20 | 0.20 | 0.20 | 0.20 | 0.20 | 0.20 | 0.20 | 0.20 |
| Xanthan gum | 1.00 | 1.00 | 1.00 | 1.00 | 1.00 | 1.00 | 1.00 | 1.00 | 1.00 |
| Sodium fluoride | 0.22 | 0.22 | 0.22 | 0.22 | 0.22 | 0.22 | 0.22 | 0.22 | 0.22 |
| Vitamin E | 0.20 | 0.20 | 0.20 | 0.20 | 0.20 | 0.20 | 0.20 | 0.20 | 0.20 |
| Flavoring | 0.50 | 0.50 | 0.50 | 0.50 | 0.50 | 0.50 | 0.50 | 0.50 | 0.50 |
| Purified water | 49.88 | 49.88 | 49.68 | 44.88 | 45.10 | 44.90 | 51.88 | 49.88 | 49.88 |

(2) Measurement of Transparency of Toothpaste

For toothpaste prepared as Examples 1 to 3 and Comparative examples 1 to 6 of the above Table 1, after adding toothpaste in a thickness of 1 cm to a transparent petri dish, transparency of toothpaste was determined by readability of the word Batang font 10 points. The result was described in Table 2.

In the evaluation of the readability, the case that the readability was impossible at a certain level based on reading letters correctly by a group of five evaluators was determined as opaque.

TABLE 2

|  | Example 1 | Example 2 | Example 3 | Comparative example 1 | Comparative example 2 | Comparative example 3 | Comparative example 4 | Comparative example 5 | Comparative example 6 |
| --- | --- | --- | --- | --- | --- | --- | --- | --- | --- |
| transparency | transparent | transparent | transparent | opaque | opaque | opaque | opaque | opaque | opaque |

In case of Comparative examples 1 to 3 containing an abrasive, they were opaque even solubilizing non-aqueous ingredients by a solubilizer, and in case of Comparative example 4, it was opaque, as there was no solubilizing process even it did not contain an abrasive.

On the other hand, in case of Examples 1 to 3 which did not comprise an abrasive and comprised a solubilizer, HCO40 or poloxamer 407, toothpaste compositions in a transparent formulation could be obtained.

In addition, in case of Comparative example 5 and Comparative example 6, which did not comprise an abrasive and comprised a solubilizer, but comprised polysorbate 20 or octyldoceceth-16, it was not possible to obtain a toothpaste composition in a transparent formulation.

Preparative Example 2 of Pumping Type Toothpaste Composition (1) Ingredients and Composition Ratio Toothpaste compositions of examples and comparative examples were prepared by the ingredients and weights shown in the following Table 3. For example, other ingredients except for an abrasive and selectively a pharmaceutical agent were primarily mixed. Then, non-aqueous ingredients, a flavoring and vitamin E were primarily mixed by adding a solubilizer, HCO40, poloxamer 407, or a mixture thereof together. Next, the abrasive such as silica or the like and selectively the pharmaceutical agent were added and were mixed under vacuum for secondary mixing to prepare toothpaste compositions. However, Comparative example 1 not using a solubilizer was prepared without the primary mixing process.

Comparative example 1 of which refractive index of the abrasive was similar to that of the liquid raw material, but did not comprise a solubilizer, showed a slightly transparent level, but on the other hand, Comparative examples 2-4 of which refractive indexes of the abrasive and liquid raw material were not similar were opaque despite of comprising a solubilizer, and Examples 1-3 of which refractive indexes of the abrasive and liquid raw material were similar and solubilized non-aqueous ingredients, particularly, a flavoring by a solubilizer, were transparent. Through this, it was confirmed that the transparency of a formulation was increased, when the refractive index of an abrasive was similar to that of a liquid raw material and non-aqueous ingredients including a flavoring were solubilized by a solubilizer, in the toothpaste composition comprising an abrasive.

(3) Confirmation of Refractive Indexes According to Glycerin Contents

The refractive indexes according to the content of glycerin to water were shown in the FIGURE. Referring to that the refractive index of silica (Solvay, Tixosil73K) was 1.437 and the FIGURE, it was confirmed that when using silica in an amount of 14% by weight, the content of glycerin to water which could make the refractive index of the liquid raw material similar was 76%. Accordingly, it was confirmed that when using silica of 14% by weight, glycerin of 62% by weight and water of about 19% by weight, the refractive indexes between ingredients of the toothpaste

TABLE 3

|  | Example 1 | Example 2 | Example 3 | Comparative example 1 | Comparative example 2 | Comparative example 3 | Comparative example 4 |
| --- | --- | --- | --- | --- | --- | --- | --- |
| Precipitated silica | 14 | 14 | 14 | 14 | 5 | 5 | 5 |
| Glycerin | 62 | 62 | 62 | 62 | 45 | 45 | 45 |
| Sodium lauryl sulfate | 1.00 | 1.00 | 1.00 | 1.00 | 1.00 | 1.00 | 1.00 |
| HCO40 | 2.00 | 0 | 1.10 | 0 | 1.10 | 2.00 | 0 |
| Poloxamer 407 | 0 | 2.00 | 1.10 | 0 | 1.10 | 0 | 2.00 |
| Sodium saccharin | 0.20 | 0.20 | 0.20 | 0.20 | 0.20 | 0.20 | 0.20 |
| Xanthan gum | 1.00 | 1.00 | 1.00 | 1.00 | 1.00 | 1.00 | 1.00 |
| Sodium fluoride | 0.22 | 0.22 | 0.22 | 0.22 | 0.22 | 0.22 | 0.22 |
| Vitamin E | 0.20 | 0.20 | 0.20 | 0.20 | 0.20 | 0.20 | 0.20 |
| Flavoring | 0.50 | 0.50 | 0.50 | 0.50 | 0.50 | 0.50 | 0.50 |
| Purified water | 18.88 | 18.88 | 18.68 | 20.88 | 44.68 | 44.88 | 44.88 |

(2) Comparison of Toothpaste Transparency

For toothpaste prepared as Examples 1 to 3 and Comparative examples 1 to 4 of the above Table 3, after adding toothpaste in a thickness of 1 cm to a transparent petri dish, transparency of toothpaste was determined by readability of the word Batang font 10 points. The result was described in Table 4.

In the evaluation of the readability, the case that the readability was impossible at a certain level based on reading letters correctly by a group of five evaluators was determined as 'opaque', and the case that identification of letters was possible but unclear as 'slightly transparent' and the case that letters could be identified without inconvenience as 'transparent'.

composition was made similar, and therefore the transparency of the toothpaste was improved.

The invention claimed is:

1. A transparent toothpaste composition to be contained in a pumping type container,
   which comprises a surfactant having HLB 14-23 as a solubilizer and an abrasive,
   wherein the solubilizer is comprised in an amount from about 0.7 to about 3% by weight based on the total weight of the composition,
   wherein the abrasive is comprised in an amount of less than 1% by weight based on the total weight of the composition, and

TABLE 4

|  | Example1 | Example2 | Example3 | Comparative example1 | Comparative example2 | Comparative example3 | Comparative example4 |
| --- | --- | --- | --- | --- | --- | --- | --- |
| transparency | transparent | transparent | tansparent | slightly transparent | opaque | opaque | opaque | wherein the abrasive has a refractive index from about 1.420 to about 1.465.

2. The transparent toothpaste composition according to claim 1,
wherein the solubilizer comprises polyoxyethylene hydrogenated castor oil, poloxamer, polyglyceryl-3-methyl glucose distearate, Oleth-10, Oleth-10/polyoxyl 10 oleyl ester NF, cereth-10, PEG-8 laurate, cocamide MEA, or mixtures thereof.

3. The transparent toothpaste composition according to claim 1,
wherein the toothpaste composition comprises a non-aqueous ingredient including vitamin E, flavoring or a mixture thereof; hydrophilic colloid including carboxymethyl cellulose, sodium alginate, xanthan gum or a mixture thereof; or a mixture thereof.

4. The transparent toothpaste composition according to claim 1, wherein the pumping type container is a transparent container.

* * * * *